(12) United States Patent
Storz et al.

(10) Patent No.: US 7,133,130 B2
(45) Date of Patent: Nov. 7, 2006

(54) METHOD FOR SCANNING MICROSCOPY, SCANNING MICROSCOPE, AND APPARATUS FOR CODING AN ILLUMINATING LIGHT BEAM

(75) Inventors: Rafael Storz, Heidelberg (DE); Volker Seyfried, Nussloch (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 416 days.

(21) Appl. No.: 10/458,958

(22) Filed: Jun. 11, 2003

(65) Prior Publication Data

US 2003/0226977 A1 Dec. 11, 2003

(30) Foreign Application Priority Data

Jun. 11, 2002 (DE) ................. 102 25 838

(51) Int. Cl.
*G01J 3/30* (2006.01)
(52) U.S. Cl. .................................. 356/317
(58) Field of Classification Search ............. None
See application file for complete search history.

(56) References Cited

U.S. PATENT DOCUMENTS

| | | | | |
|---|---|---|---|---|
| 3,916,205 A * | 10/1975 | Kleinerman | ............. | 356/36 |
| 5,123,731 A * | 6/1992 | Yoshinaga et al. | ............. | 356/73 |
| 5,371,368 A * | 12/1994 | Alfano et al. | ............. | 250/341.1 |
| 5,735,276 A * | 4/1998 | Lemelson | ............. | 250/458.1 |
| 5,940,177 A * | 8/1999 | Esser et al. | ............. | 356/338 |
| 6,376,843 B1 * | 4/2002 | Palo | ............. | 250/458.1 |
| 6,744,525 B1 * | 6/2004 | Goltsos | ............. | 356/614 |
| 6,897,954 B1 * | 5/2005 | Bishop et al. | ............. | 356/317 |
| 6,900,899 B1 * | 5/2005 | Nevis | ............. | 356/484 |
| 6,961,124 B1 * | 11/2005 | Engelhardt et al. | ............. | 356/417 |
| 6,963,398 B1 * | 11/2005 | Sasaki et al. | ............. | 356/318 |

FOREIGN PATENT DOCUMENTS

| | | |
|---|---|---|
| DE | 197 13 254 | 10/1998 |
| DE | 19902625 | 9/1999 |
| WO | WO 92/02839 | 2/1992 |

* cited by examiner

Primary Examiner—Gregory J. Toatley, Jr.
Assistant Examiner—Juan Valentin
(74) Attorney, Agent, or Firm—Darby & Darby

(57) ABSTRACT

In a method for scanning microscopy an illuminating light beam that contains at least first light of a first wavelength and second light of a second wavelength, is coded. The coded illuminating light beam is directed onto a specimen and detection light proceeding from the specimen is decoded.

21 Claims, 9 Drawing Sheets

METHOD FOR SCANNING MICROSCOPY, SCANNING MICROSCOPE, AND APPARATUS FOR CODING AN ILLUMINATING LIGHT BEAM

CROSS REFERENCE TO RELATED APPLICATIONS

This application claims priority to German patent application 102 25 838.4, the subject matter of which is hereby incorporated by reference herein.

FIELD OF THE INVENTION

The invention concerns a method for scanning microscopy.

The invention additionally concerns a scanning microscope having at least one light source for generating an illuminating light beam that is directable onto a specimen and contains at least first light of a first wavelength and second light of a second wavelength.

The invention further concerns an apparatus for coding an illuminating light beam, which apparatus can also be used outside or independently of scanning microscopy.

BACKGROUND OF THE INVENTION

In scanning microscopy, a specimen is illuminated with a light beam in order to observe the reflected or fluorescent light emitted from the specimen. The focus of an illuminating light beam is moved in a specimen plane by means of a controllable beam deflection device, generally by tilting two mirrors; the deflection axes are usually perpendicular to one another, so that one mirror deflects in the X direction and the other in the Y direction. Tilting of the mirrors is brought about, for example, by means of galvanometer positioning elements. The power level of the light coming from the specimen is measured as a function of the position of the scanning beam. The positioning elements are usually equipped with sensors to ascertain the present mirror position.

In confocal scanning microscopy specifically, a specimen is scanned in three dimensions with the focus of a light beam.

A confocal scanning microscope generally comprises a light source, a focusing optical system with which the light of the source is focused onto an aperture (called the "excitation pinhole"), a beam splitter, a beam deflection device for beam control, a microscope optical system, a detection pinhole, and the detectors for detecting the detected or fluorescent light. The illuminating light is coupled in via a beam splitter. The fluorescent or reflected light coming from the specimen travels back through the beam deflection device to the beam splitter, passes through it, and is then focused onto the detection pinhole behind which the detectors are located. Detection light that does not derive directly from the focus region takes a different light path and does not pass through the detection pinhole, so that a point datum is obtained which results, by sequential scanning of the specimen, in a three-dimensional image. A three-dimensional image is usually achieved by acquiring image data in layers, the track of the scanning light beam on or in the specimen ideally describing a meander (scanning one line in the X direction at a constant Y position, then stopping the X scan and slewing by Y displacement to the next line to be scanned, then scanning that line in the negative X direction at constant Y position, etc.). To allow image data acquisition in layers, the specimen stage or the objective is shifted after a layer has been scanned so that the next layer to be scanned is brought into the focal plane of the objective.

For many applications, specimens are prepared with several markers, for example several different fluorescent dyes. These dyes can be excited sequentially, for example using illuminating light beams that exhibit different excitation wavelengths. Simultaneous excitation using an illuminating light beam that contains light of several excitation wavelengths is also common. European Patent Application EP 0 495 930: "Confocal microscope system for multi-color fluorescence," for example, discloses an arrangement having a single laser that emits several laser lines. At present, such lasers are usually embodied in practical terms as mixed-gas lasers, in particular as Ar/Kr lasers.

When the acquired image data are analyzed, it is important to be able to make an allocation as to which detected signals are attributable to which marker or fluorescent dye. This functions particularly reliably and reproducibly if each fluorescent dye possesses an emission spectrum specific to it, which does not overlap with any of the other emission spectra. In such a case the individual fluorescent dyes can be excited simultaneously, and the detection light, spectrally divided in accordance with the individual fluorescent dyes, reflects the distribution of the individual fluorescent dyes in the specimen. A multi-band detector such as the one known, for example, from German Unexamined Application DE 199 02 625 A1 is often used for detection in this context.

If the emission spectra of the individual fluorescent dyes do overlap, however, the distributions of the individual fluorescent dyes in the specimen can no longer be cleanly optically separated from one another, although a certain degree of separation of the dyes can be achieved, based on the acquired data, using mathematical methods.

SUMMARY OF THE INVENTION

It is therefore an object of the invention to provide a method for scanning microscopy that reliably and efficiently makes possible an allocation of measured detected signals to different fluorescent dyes in a specimen, in particular even when the emission spectra of the fluorescent dyes overlap.

The invention provides a method for scanning microscopy comprising the steps of:

generating an illuminating light beam that contains at least first light of a first wavelength and second light of a second wavelength, at least the first light comprising a coding;

illuminating a specimen with the illuminating light beam; and decoding the detection light proceeding from the specimen.

A further object of the invention is to provide a scanning microscope with which it is possible, reliably and efficiently, to allocate measured detected signals to different fluorescent dyes in a specimen, in particular even when the emission spectra of the fluorescent dyes overlap.

This invention also provides a scanning microscope comprising at least one light source for generating an illuminating light beam that is directable onto a specimen and that contains at least first light of a first wavelength and second light of a second wavelength, a coding apparatus for coding at least the first light, and a decoding apparatus for decoding the detection light proceeding from the specimen.

An additional object of the invention is to provide an apparatus for coding an illuminating light beam that contains at least first light of a first wavelength and second light of a second wavelength.

The invention further provides an apparatus for coding comprising a beam splitter that splits the illuminating light beam into a first and a second sub-beam, a beam combiner that at least partially combines the first and the second sub-beam, are provided, and an acoustooptical component or an electrooptical component acting at least on the first sub-beam.

The invention has the advantage that in the context of specimens stained with several fluorescent dyes, the various fluorescent dyes can be easily and efficiently distinguished from one another in the acquired images.

By means of suitable coding and associated subsequent decoding of the simultaneously irradiated excitation light sources, a further distinguishing feature of the individual fluorescent dyes can be utilized, namely the fact that as a rule, the excitation spectra of the individual fluorescent dyes also differ from one another. The method proves to be particularly simple—although it is not limited to this special case—if the first light and the second light, which exhibit different wavelengths, each also excite only a single one of the fluorescent dyes present in the specimen. The allocation of detected fluorescent light to a specific excitation wavelength then also automatically means allocation to a specific fluorescent dye, so that the distribution of the individual fluorescent dyes in the specimen can be determined directly. To achieve this, however, it must be possible to allocate each of the individual components of the detected fluorescent light to the associated excitation wavelengths. To make this possible, the information as to which light component of the illuminating light beam has generated the fluorescent light must be present in coded form in the detection light.

In a specific embodiment, the specimen contains a first fluorescent dye that is excitable with the first light, and a second fluorescent dye that is excitable with the second light.

In a preferred embodiment, the method according to the present invention encompasses the further steps of identifying a first component of the detection light that proceeds from the first fluorescent dye, and identifying at least a second component of the detection light that proceeds from the second fluorescent dye.

Coding of the illuminating light beam can be accomplished in various ways, and is thus adaptable to the individual requirements of the specimen to be examined and the experiments to be performed.

In a preferred variant, the coding encompasses a time-related coding of the pulse train period of an illuminating light beam that is pulsed at least in terms of the first light.

For time-related coding, the light source that generates the illuminating light beam preferably encompasses several pulsed lasers that, in continuous repetition, consecutively, and at different times in succession, emit light pulses which exhibit different excitation wavelengths. Time-related coding is accomplished, for example, by triggering different pulsed lasers, laser diodes, or LEDs in time-delayed synchronized fashion. It is also possible, for example using optically parametric oscillators (OPOs) or optically parametric amplifiers (OPAs) or lasers operating simultaneously at several wavelengths, to generate different excitation wavelengths simultaneously and in pulsed fashion and then to generate a time delay, for example, using different path lengths, so that the coding contains a definition of a chronological sequence of the pulses of the first and the second light. The light having the coded light components (first light, second light, etc.) of different excitation wavelengths is combined, and is used in the scanning microscope or confocal scanning microscope for specimen excitation.

In another variant, the coding contains an amplitude coding whose profile over time can be recognized upon decoding.

In a preferred embodiment, the coding contains a frequency coding. Frequency coding can be implemented in various ways.

For frequency coding, the different components of the illuminating light beam having different excitation wavelengths can each be modulated with a different frequency. This can be done by individually modulating the individual light components (e.g. by means of acoustooptical, electrooptical, mechanical, etc. modulators) and then combining their light. In another preferred embodiment, the already-combined light of the different excitation wavelengths is frequency-modulated in wavelength-dependent fashion. The fluorescent light, consequently also frequency-modulated, can be broken down into the components belonging to the individual frequencies (i.e. the excitation wavelengths) by a decoding procedure using ordinary demodulators (e.g. based on radio technology or lock-in amplifiers, or digitally after A/D conversion).

An advantageous apparatus for coding and modulation exploits the fact that when light is diffracted at traveling waves, a pulse transfer to the light wave takes place, and the frequency of the diffracted light is modified by the diffraction. A diffraction of this kind at traveling waves occurs, as already mentioned, in acoustooptical components.

In a preferred embodiment, the coding apparatus for frequency coding contains an acoustooptical component or an electrooptical modulator. The acoustooptical component is preferably configured as an acoustooptical filter (AOTF). Acoustooptical filters are widely known; German Unexamined Application DE 197 13 254 may be mentioned simply by way of example in this context. In acoustooptical modulators (acoustooptical tunable filters, AOTFs), an acoustic generator, for example a piezoelement, which is activated by an electromagnetic control frequency, generates an acoustic wave which passes through the AOTF and at which a light wave can be diffracted. Ideally, acoustooptical filters are configured in such a way that only the component having the wavelength corresponding to the control frequency is separated by diffraction from the rest of the incident light.

An AOTF diffracts only light of certain wavelengths: the wavelength of the diffracted light can be defined by the frequency of the acoustic wave irradiated into the acoustooptical crystal, and the diffraction efficiency is determined by the amplitude of the irradiated acoustic wave. Not only it is possible with an AOTF to deflect only certain wavelengths, but the wavelength of the deflected light also changes, typically on the order of ca. 10 to 100 MHz; the wavelength change depends on the frequency of the acoustic wave injected into the AOTF, which in turn depends on the deflected wavelength. In other words, the wavelength change is different for each wavelength.

In a preferred embodiment of the scanning microscope and of the apparatus for coding an illuminating light beam, a beam splitter is provided that splits the illuminating light beam into a first and a second sub-beam; and a beam combiner is provided that at least partially combines the first and the second sub-beam, the acoustooptical component acting on the first sub-beam. In a variant, a further acoustooptical component can be provided that acts on the second sub-beam. The acoustooptical components are preferably configured as AOTFs, so that the illuminating light beam can theoretically contain any number of light components of different wavelengths without causing problems due to differing deflection angles upon recombination using the beam combiner. The beams of one wavelength combined with one another now beat with each other, so that for light of each excitation wavelength a sinusoidal modulation is obtained whose modulation frequency corresponds to the associated frequency of the acoustic wave irradiated into the acoustooptical crystal. The intensity modulation is consequently different for all light components of differing excitation wavelengths. In a preferred embodiment, the acoustooptical component can additionally act as a beam splitter.

The detection light occurring in the specimen, which as a rule is fluorescent light, is preferably detected using the detectors usual in scanning microscopy (e.g. photomultipliers), and converted into electrical detected signals whose amplitude is proportional to the detection light power level. The detection light or detected signals are decoded upon time-related decoding by utilizing the time-related information as to when the individual excitation wavelengths arrived at the specimen. For this purpose, it is useful for the coding unit to transmit a synchronization signal (e.g. the triggers that start the individual excitation lasers) to the decoding unit. Time-related decoding can consist either in that the detected signal is distributed into different channels in a demultiplexer unit, or that for each wavelength, a gated integrator (e.g. gated charge amplifier, boxcar averager, etc.) performs an analog or digital integration of the signal within the time intervals belonging to the corresponding excitation wavelength. It is useful if the distance in time of the laser pulses of the individual wavelengths is selected to be greater than the emission duration of the fluorescent dyes (usually approx. 10 ns), so that decoding functions optimally.

In another preferred embodiment, the decoding is accomplished digitally, for example in a computer. For that purpose, the decoding apparatus contains an analog-digital converter that performs an analog-digital conversion of the detected signals.

The decoding preferably encompasses a fitting to a definable function, which is advantageous especially in the context of frequency coding. This can be accomplished in both digital and (particularly quickly and efficiently) analog fashion.

In another variant embodiment, the decoding encompasses a Fourier transform.

In a preferred embodiment, the decoding apparatus is synchronized with the coding apparatus.

In a preferred embodiment, the scanning microscope is a confocal scanning microscope. Coding is also of particular interest especially when the fluorescent light is detected in the confocal microscope using a matrix detector (CCD or the like) (e.g. Nipkow disk systems or conventional microscope systems in which confocality is achieved by deconvolution), since in this case spectral separation of the emissions of the various fluorescent dyes is usually difficult or impossible.

BRIEF DESCRIPTION OF THE DRAWINGS

The subject matter of the invention is depicted schematically in the drawings and will be described below with reference to the Figures, identically functioning elements being labeled with the same reference characters. In the drawings.

DETAILED DESCRIPTION OF THE INVENTION

Figure 1:
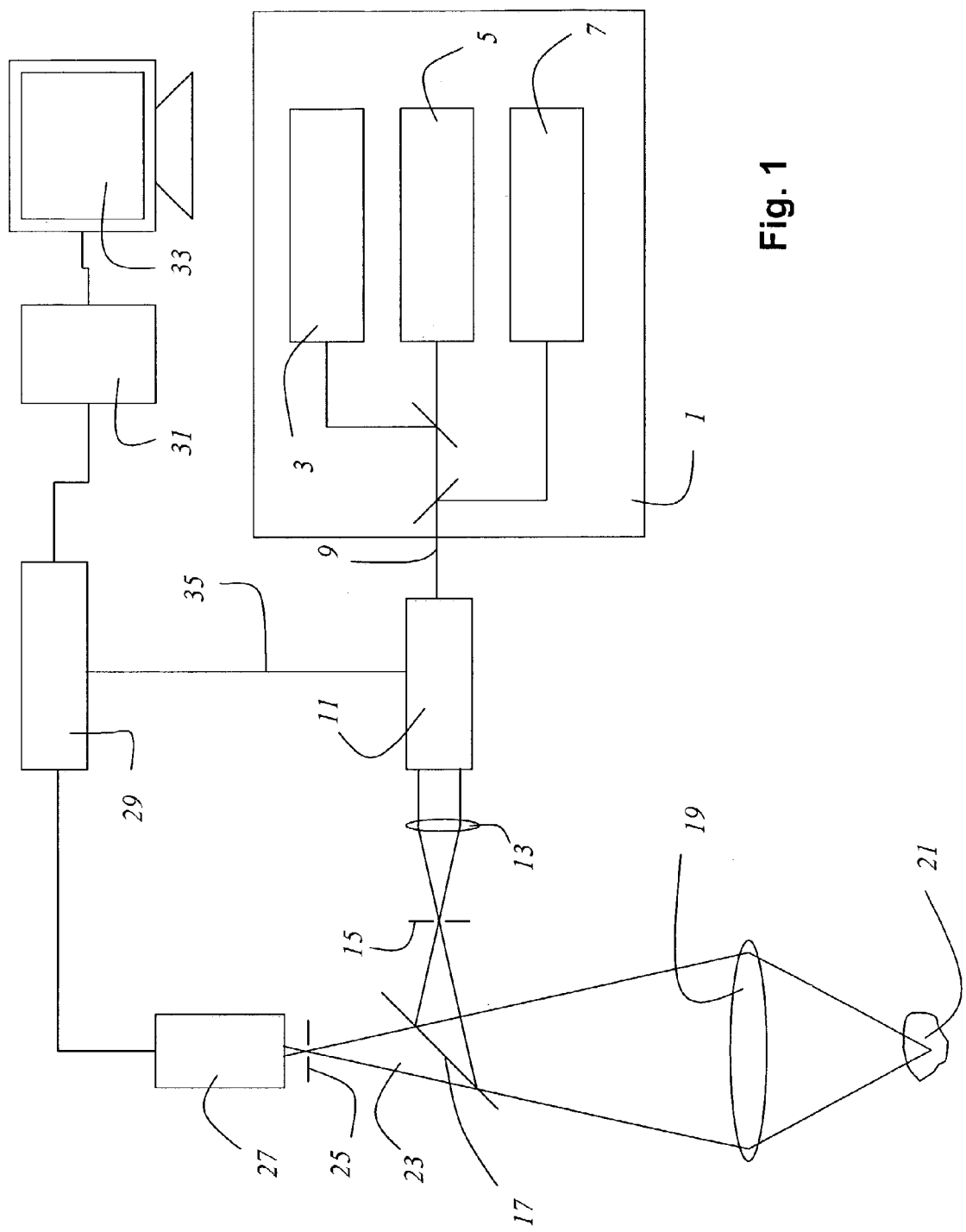
FIG. 1 shows a scanning microscope according to the present invention.

FIG. 1 schematically shows a confocal scanning microscope according to the present invention that is embodied as a confocal scanning microscope. Illuminating light beam 9, coming from a light source 1 that contains a first laser 3 which emits excitation light of a first wavelength, a second laser 5 which emits excitation light of a second wavelength, and a third laser 7 which emits excitation light of a third wavelength, is coded using a coding apparatus 11 and focused by means of optical system 13 onto illuminating pinhole 15. Combination of the individual light beams emitted by the lasers occurs in light source 1 using dichroic beam combiners. After passing through illumination pinhole 15, illuminating light beam 9 is focused by a beam splitter 17 via microscope optical system 19 onto specimen 21. In the interest of better clarity, further usual elements for beam guidance and beam shaping, for example the scanning apparatus, scanning optical system, or tube optical system, are not shown. These are, however, familiar to one skilled in the art. Specimen 21 is labeled with three fluorescent dyes. In the case of non-transparent specimens 21, illuminating light beam 9 is guided over the specimen surface. With biological specimens 21 (preparations) or transparent specimens, illuminating light beam 9 can also be guided through specimen 21. Detection light beam 23 proceeding from specimen 21 travels through microscope optical system 19 to beam splitter 17, passes through it and, after passing through detection pinhole 25, strikes a detector 27, which is embodied as a photomultiplier and which generates electrical detected signals 21 whose amplitude is proportional to the power level of the detection light. The detected signals are transferred to a decoding apparatus 29 that is synchronized with coding apparatus 11 via line 35. "Synchronization" in this case means that information regarding the coding caused by the coding apparatus is transferred to decoding apparatus 29. It is also conceivable, however, for the information flow also to occur in the opposite direction. In the decoding apparatus, an allocation is made as to which detected signals were caused by which light component of illuminating light beam 9. These data are transferred to a PC 31 and displayed to the user in graphically processed fashion on a monitor 33.

Figure 2:
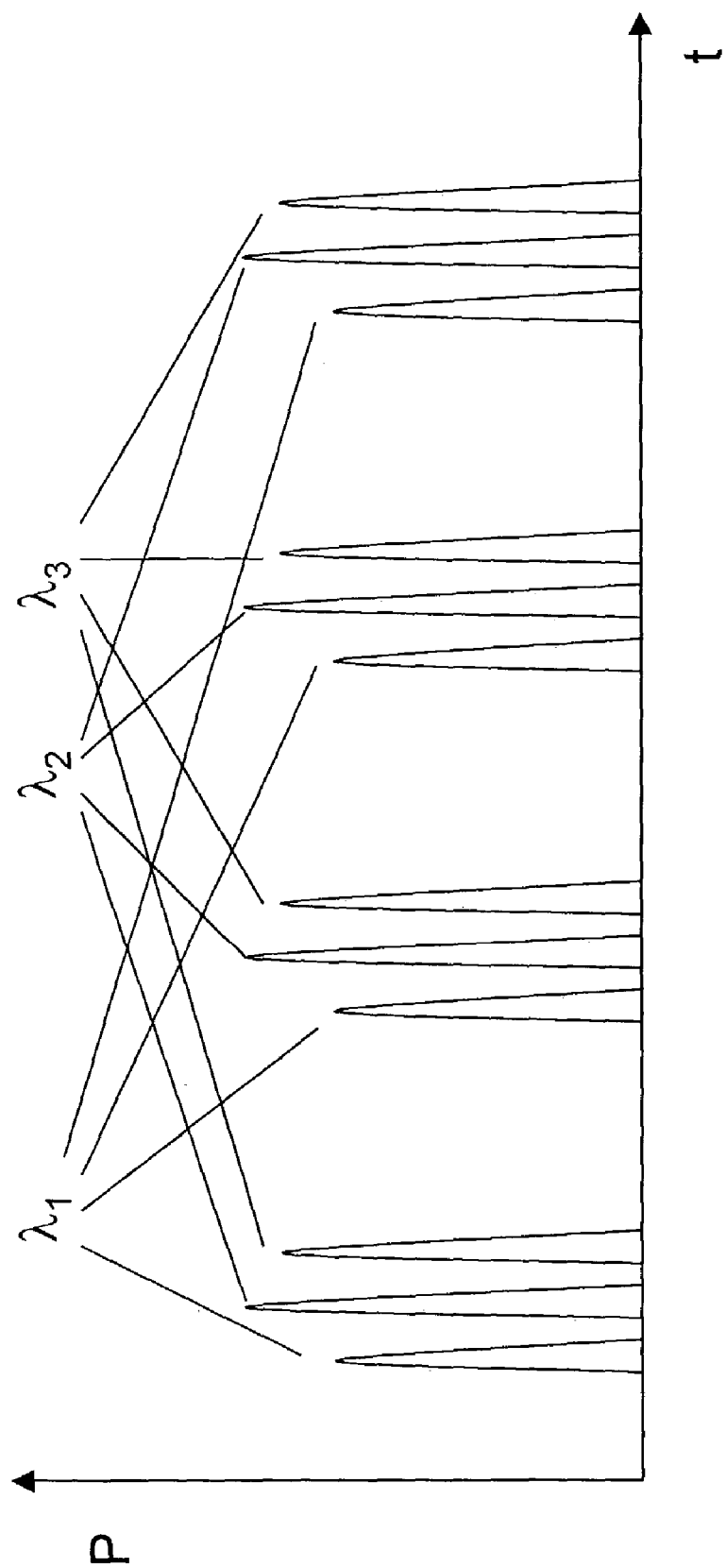
FIG. 2 schematically depicts a time-related coding.

FIG. 2 schematically depicts a time-related coding that contains a definition of a chronological sequence of the pulses of a first, a second, and a third light of an illuminating light beam, the first light having a wavelength $\lambda_1$, the second light a wavelength $\lambda_2$, and the third light a wavelength $\lambda_3$. Light power level P is shown as a function of time t. All three wavelengths can be acted upon with different light power levels.

Figure 3:
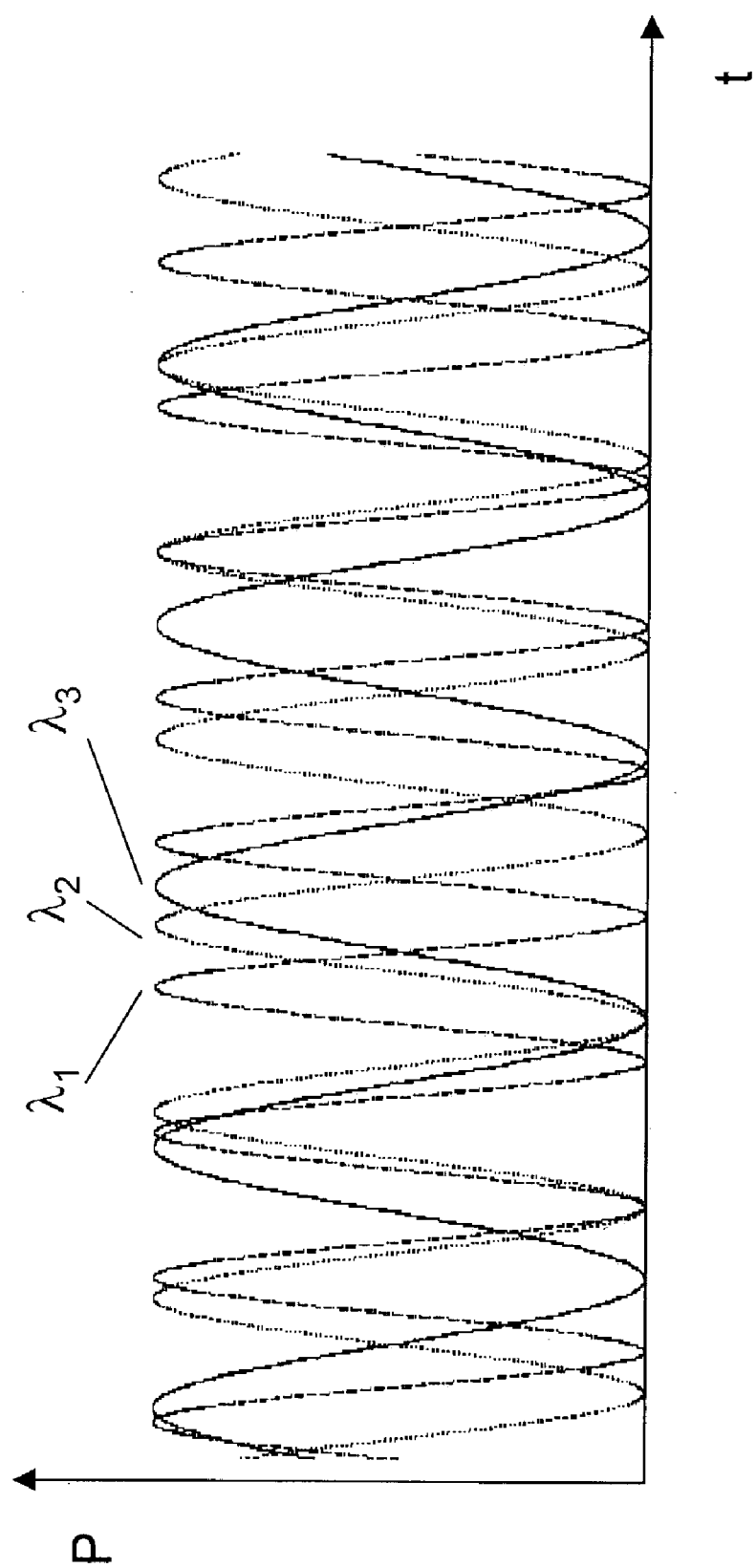
FIG. 3 schematically depicts a frequency coding.

FIG. 3 schematically depicts a frequency coding. For this, the components of an illuminating light beam of different excitation wavelengths are each modulated at a different frequency.

Figure 4:
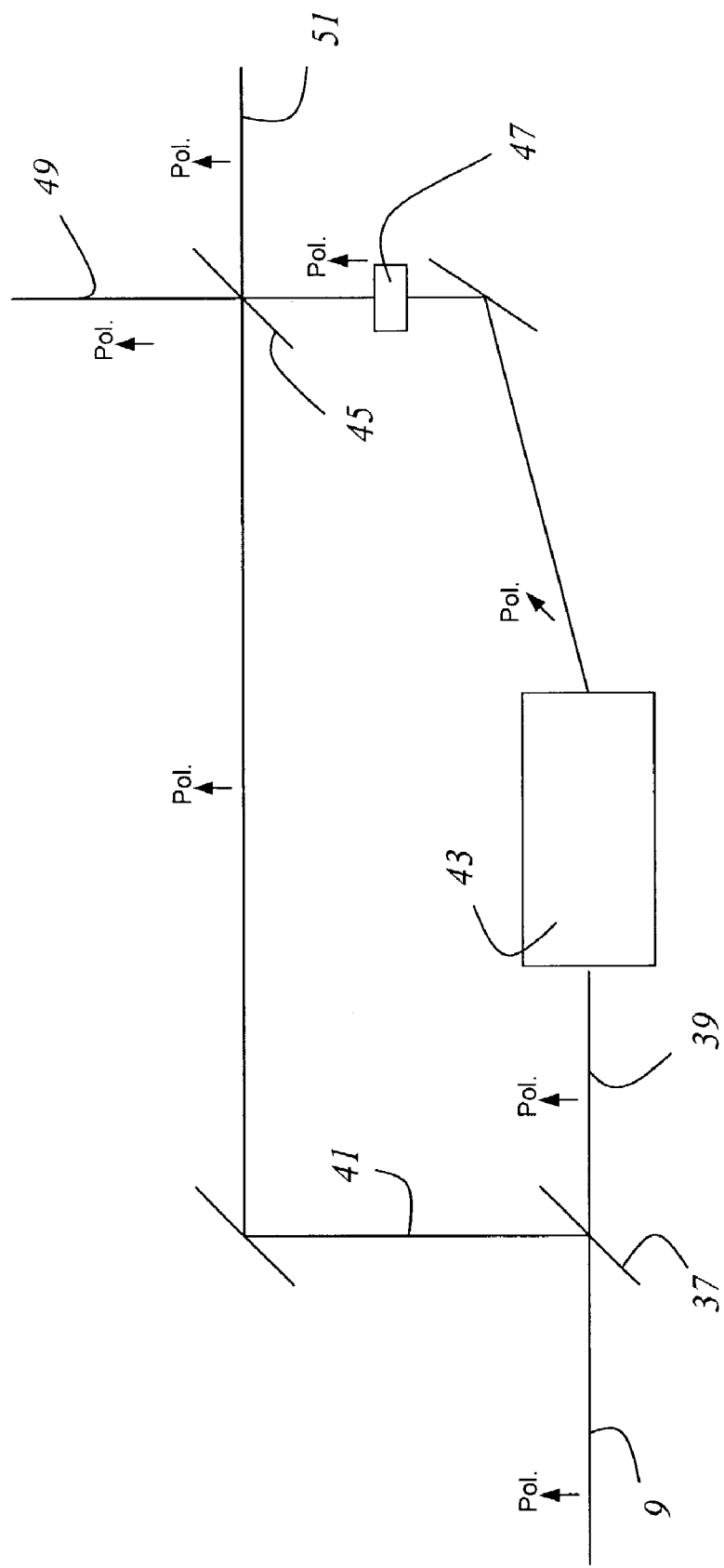
FIG. 4 shows an apparatus for modulating and/or coding an illuminating light beam.

FIG. 4 shows an apparatus for modulating and/or coding an illuminating light beam. In this variant, illuminating light beam 9, which contains all the wavelengths to be modulated, is split into a first sub-beam 39 and a second sub-beam 41 using a beam splitter 37. First sub-beam 39 is passed through an AOTF 43, the latter being activated in such a way that all the relevant wavelengths are diffracted. Upon diffraction at the traveling acoustic waves of AOTF 43, a pulse transfer to the light wave takes place, thereby modifying the wavelength of the diffracted light because of the diffraction. First sub-beam 39 and second sub-beam 41 are conveyed to a beam combiner 45 which combines the first and second sub-beam into two output beams 49, 51. Prior to recombination, first sub-beam 39 passes through a polarizing rotator unit 47, embodied as a $\lambda/2$ plate, in order to rotate the polarization back, since the AOTF used here rotates the polarization. The light components combined with one another, which originally had the same wavelength, beat with one another after combination so that a sinusoidal intensity modulation is obtained for each component of the illuminating light of one excitation wavelength. The modulation frequency of each wavelength corresponds to the associated acoustic deflection frequency, and is thus distinguished from one wavelength to another.

Figure 5:
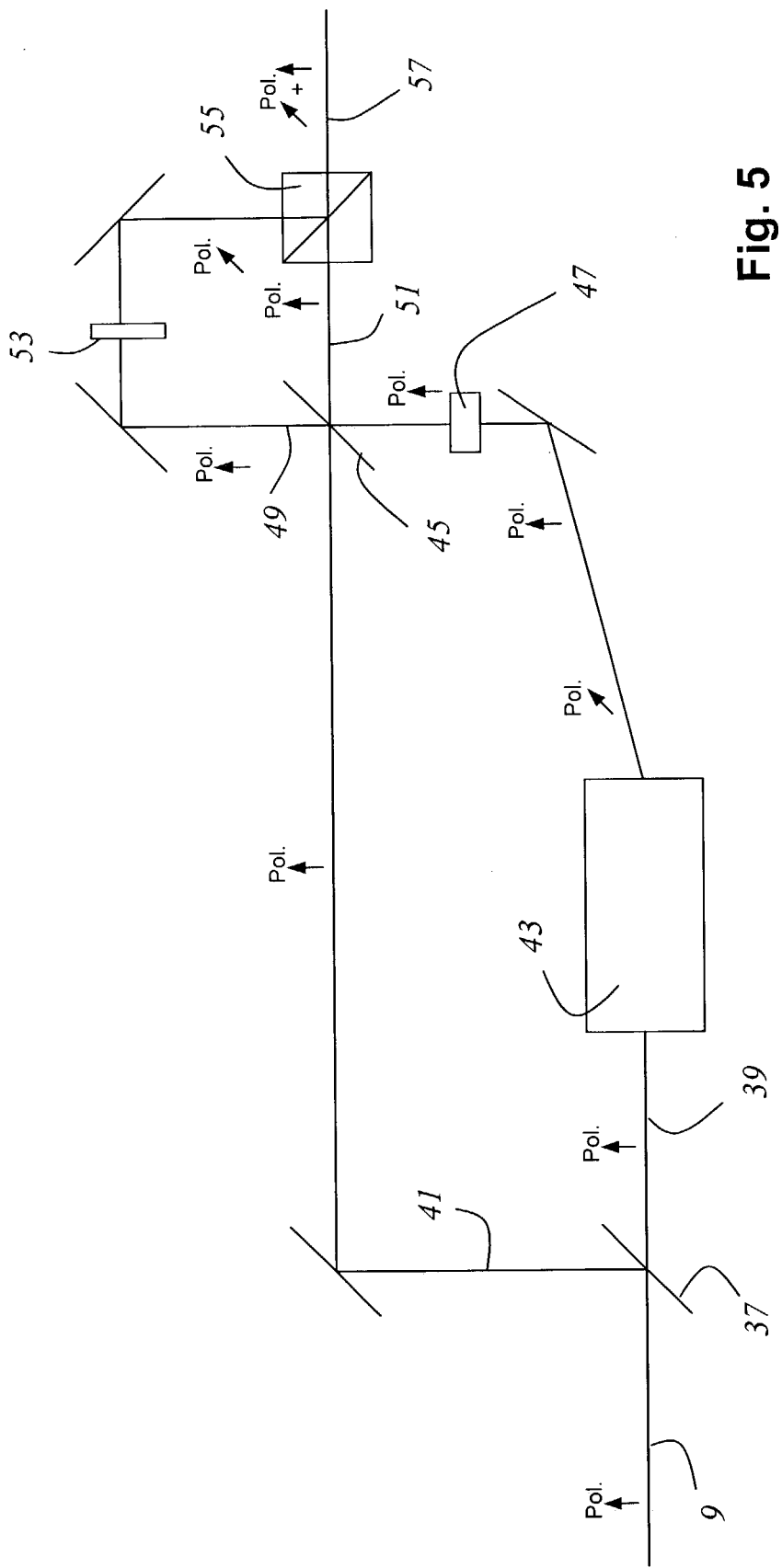
FIGS. 5 through 9 show further apparatuses for modulating and/or coding an illuminating light beam.

FIG. 5 shows a further apparatus for modulating and/or coding an illuminating light beam. This operates on the same principle as the apparatus shown in FIG. 4. Once the polarization of first output beam 49 has been rotated 90° using a further polarizing rotator unit 53, the two output beams 49, 51 are once again combined with one another using a polarizing beam combiner 55, so that ultimately no light is wasted. The resulting laser beam 57 is modulated in each of the two polarization directions (offset 90° in phase) so that the total light power level is constant over time. In polarization-retaining processes such as SHG two-photon microscopy, it is therefore generally possible to use both signal components if, in the signal detection process, both polarizations of the detection light are separately detected and decoded.

Figure 6:
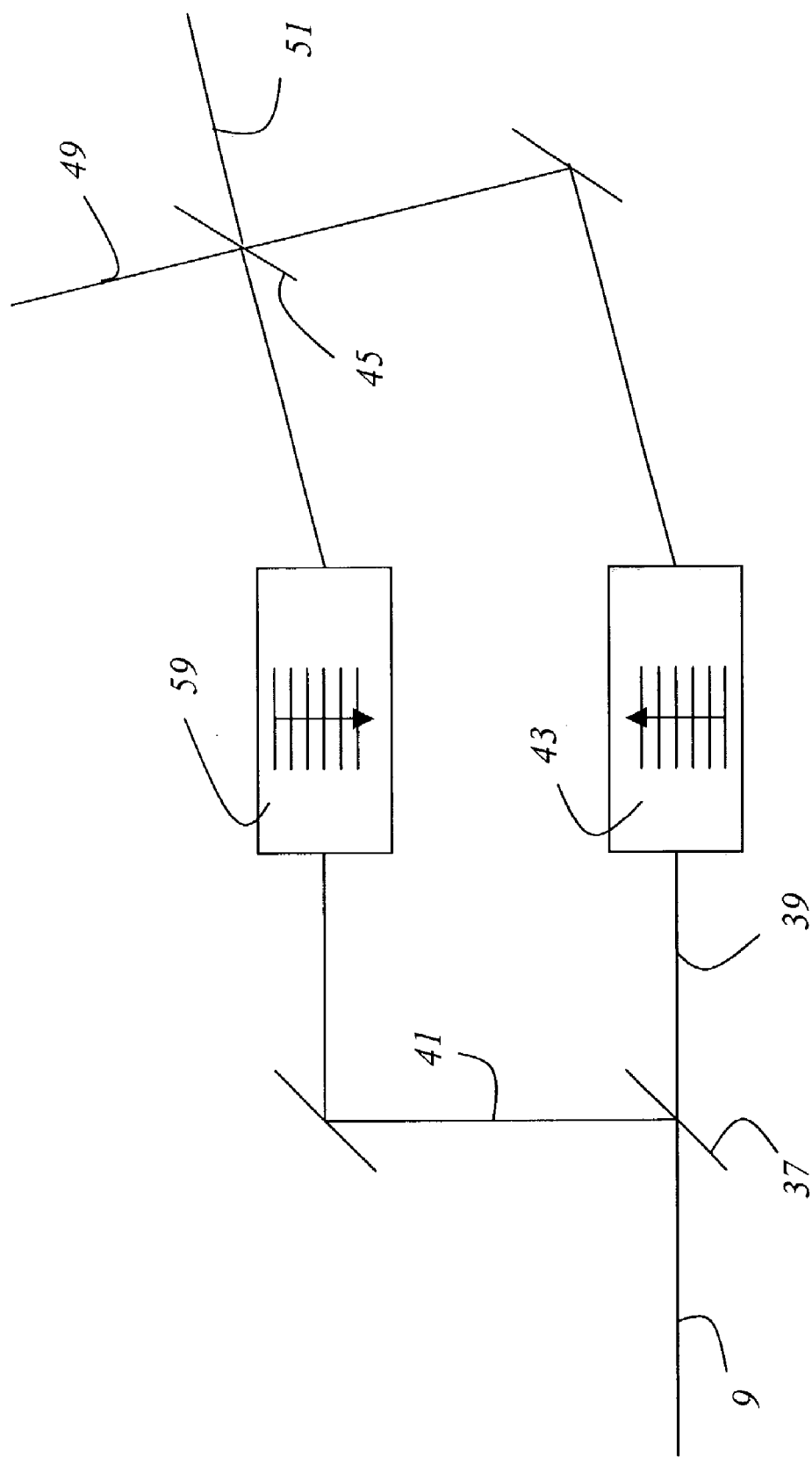

FIG. 6 shows a further apparatus for modulating and/or coding an illuminating light beam. In this apparatus, a further AOTF 59 is located in the beam path of second sub-beam 41 and increases the wavelength of second sub-beam 41, whereas AOTF 43 decreases the wavelength of first sub-beam 39 to the same degree. The acoustic waves travel through AOTF 43 and further AOTF 59 in opposite directions. The modulation frequency of output beams 49, 51 thus corresponds to twice the frequency of the acoustic waves.

Figure 7:
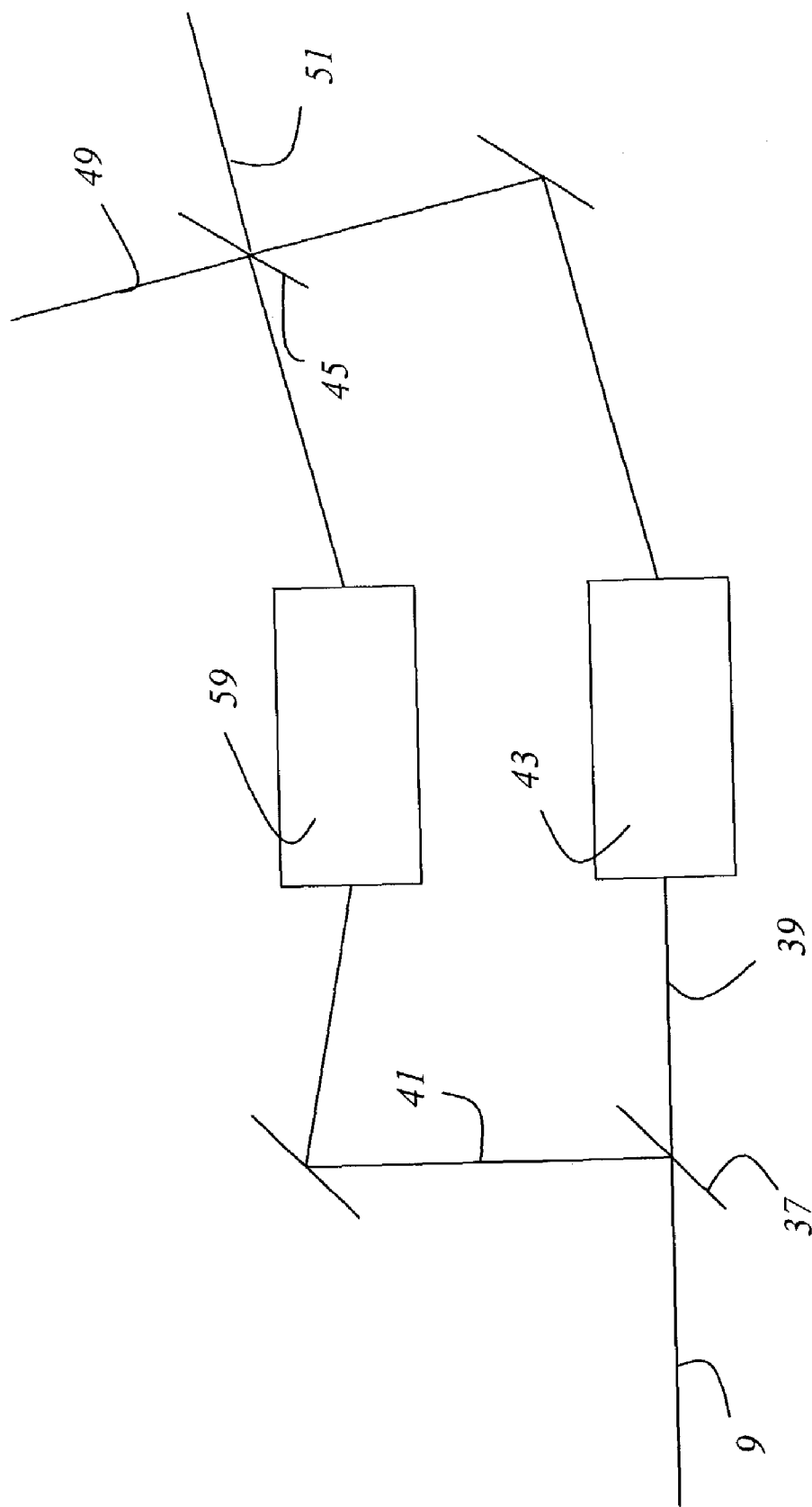

FIG. 7 shows a further apparatus for modulating and/or coding an illuminating light beam that corresponds substantially to the apparatus illustrated in FIG. 6. AOTF 43 and further AOTF 59 are, however, activated with different HF frequencies. The modulation frequency of output beams 49, 51 corresponds to the sum or difference of the frequencies of the acoustic waves.

Figure 8:
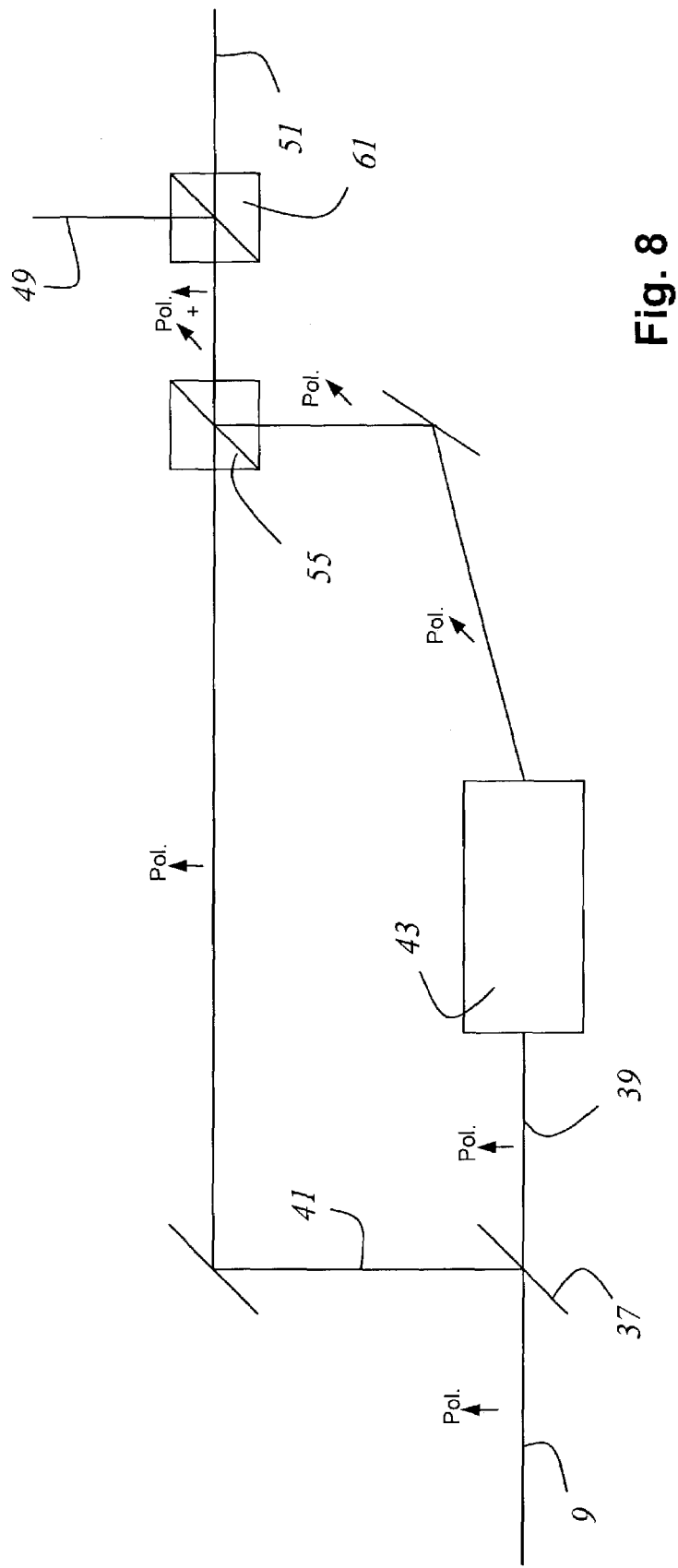

FIG. 8 shows a further apparatus for modulating and/or coding an illuminating light beam, in which combination of the first and second sub-beams 39, 41 is accomplished using a polarizing beam combiner 55; and a downstream polarizer 61, arranged at 45 degrees, causes a separation into first output beam 49 and second output beam 51, thereby mixing light of the different polarization directions.

Figure 9:
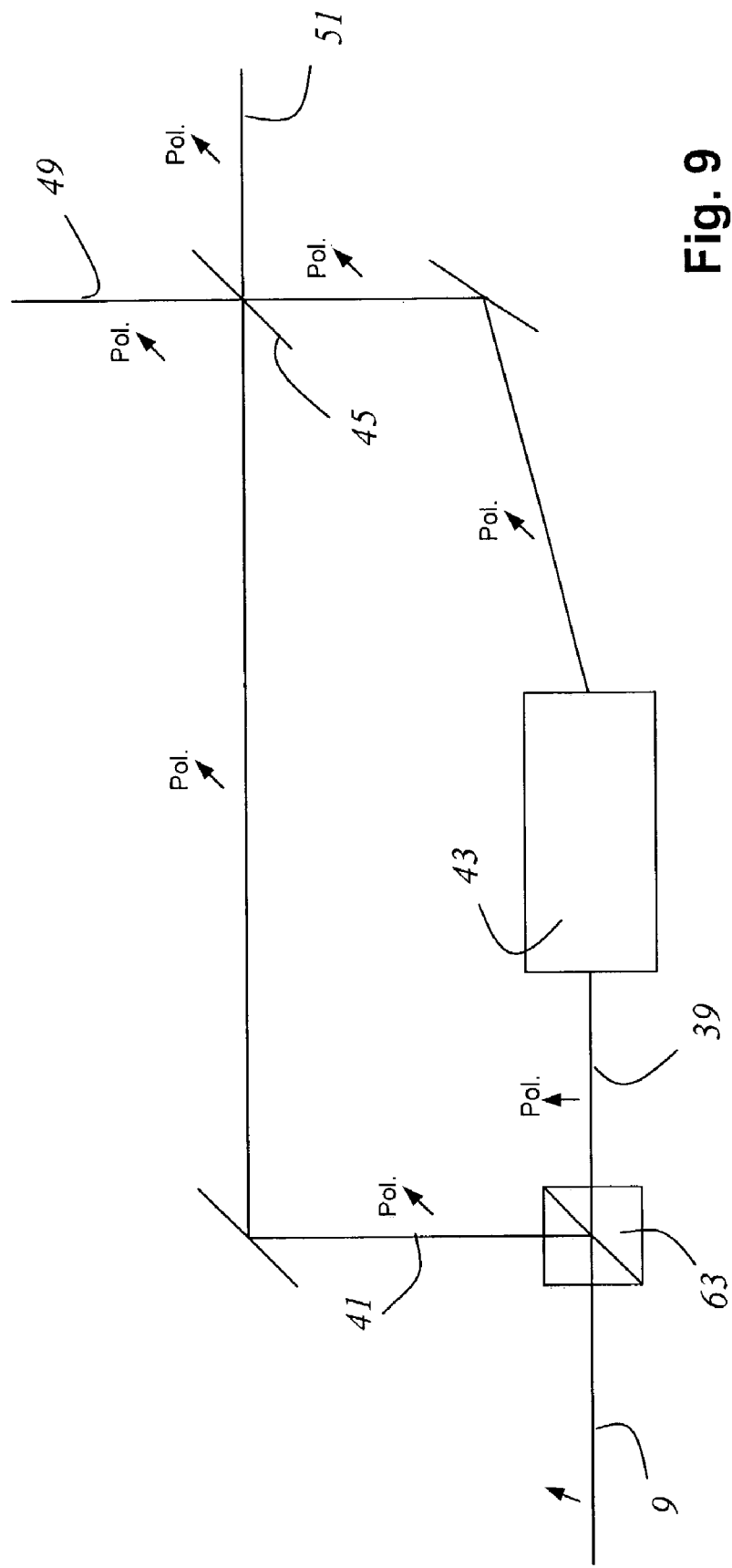

FIG. 9 shows a further apparatus for modulating and/or coding an illuminating light beam. This operates on the same principle as the apparatus shown in FIG. 4, illuminating light beam 9 strikes a polarizing beam splitter 63 with a polarization plane that is turned about 45 degrees to the splitting plane. The polarizing beam splitter 63 splits the illuminating light beam 9 into first and second sub-beams 39, 41.

The invention has been described with reference to a particular embodiment. It is self-evident, however, that changes and modifications can be made without thereby leaving the range of protection of the claims below.

What is claimed is:

1. A method for scanning microscopy comprising the steps of:
    generating an illuminating light beam that contains at least first light of a first wavelength and second light of a second wavelength, at least the first light comprising a coding;
    illuminating a specimen with the illuminating light beam, wherein the specimen contains a first fluorescent dye that is excitable with the first light and the specimen contains a second fluorescent dye that is excitable with the second light; and
    decoding the detection light proceeding from the specimen, the decoding including identifying a first component of the detection light that proceeds from the first fluorescent dye and identifying at least a second component of the detection light that proceeds from the second fluorescent dye.

2. The method as defined in claim 1, wherein the coding encompasses a time-related coding of the pulse train period of the illuminating light beam the illuminating light beam being pulsed at least in terms of the first light.

3. The method as defined in claim 1, wherein at least the first and the second light are pulsed; and the coding contains a definition of a sequence in time of the pulses of the first and the second light.

4. The method as defined in claim 1, wherein the coding contains an amplitude coding or a frequency coding.

5. The method as defined in claim 1, wherein the decoding is accomplished digitally and encompasses an analog-digital conversion.

6. The method as defined in claim 5, wherein the decoding contains a fitting to a definable function.

7. The method as defined in claim 6, wherein the decoding encompasses a Fourier transform.

8. A scanning microscope comprising at least one light source for generating an illuminating light beam that is directable onto a specimen and that contains at least first light of a first wavelength and second light of a second wavelength, a coding apparatus for coding at least the first light, and a decoding apparatus for decoding the detection light proceeding from the specimen;
wherein:
    the specimen contains a first fluorescent dye that is excitable with the first light, and the specimen contains a second fluorescent dye that is excitable with the second light; and
    the decoding includes identifying a first component of the detection light that proceeds from the first fluorescent dye and identifying at least a second component of the detection light that proceeds from the second fluorescent dye.

9. The scanning microscope as defined in claim 8, wherein the light source encompasses a pulsed laser and wherein the coding apparatus performs a time-based coding of the pulse train period of an illuminating light beam that is pulsed at least in terms of the first light.

10. The scanning microscope as defined in claim 8, wherein at least the first and the second light are pulsed; and a sequence in time of the pulses of the first and the second light is definable with the coding apparatus.

11. The scanning microscope as defined in claim 8, wherein the coding apparatus performs an amplitude coding or a frequency coding.

12. The scanning microscope as defined in claim 8, wherein the coding apparatus contains an acoustooptical component or an electrooptical modulator (EOM).

13. The scanning microscope as defined in claim 8, wherein the decoding apparatus is synchronized with the coding apparatus.

14. The scanning microscope as defined in claim 8 wherein the microscope is a confocal scanning microscope.

15. An apparatus for coding a illuminating light beam that contains at least first light of a first wavelength and second light of a second wavelength, comprising a beam splitter that splits the illuminating light beam into a first and a second sub-beam, a beam combiner that at least partially combines the first and the second sub-beam so as to code the first light and the second light without changing the respective wavelengths of the first and second light, are provided, and an acoustooptical component or an electrooptical component acting at least on the first sub-beam.

16. The apparatus as defined in claim 15, wherein the acoustooptical component modifies the wavelength of at least a portion of the illuminating light beam by diffraction at an acoustic wave.

17. The apparatus as defined in claim 15, wherein a further acoustooptical component is provided that acts on the second sub-beam.

18. The apparatus as defined in claim 15, wherein the acoustooptical component acts as a beam splitter.

19. A method for scanning microscopy comprising the steps of:
   generating an illuminating light beam that contains at least first light of a first wavelength and second light of a second wavelength, at least the first light comprising a coding;
   illuminating a specimen with the illuminating light beam; and
   decoding the detection light proceeding from the specimen, the decoding including identifying a first component of the detection light caused by the first light and identifying at least a second component of the detection light caused by the second light.

20. The method as defined in claim 19 wherein the coding includes at least one of a time-related coding of a pulse train period of the illuminating light beam, an amplitude coding and a frequency coding.

21. The method as defined in claim 19 wherein the decoding includes at least one of fitting to a definable function and a Fourier transform.

* * * * *